United States Patent [19]
Klaveness et al.

[11] Patent Number: 5,928,626
[45] Date of Patent: *Jul. 27, 1999

[54] CONTRAST AGENTS, CONSISTING OF CARBOHYDRATE PARTICLES

[75] Inventors: Jo Klaveness, Oslo; Pål Rongved, Hellvik; Lars Stubberud, Södertälje, all of Norway

[73] Assignee: Nycomed Imaging AS, Oslo, Norway

[ * ] Notice: This patent is subject to a terminal disclaimer.

[21] Appl. No.: 08/810,344

[22] Filed: Feb. 27, 1997

Related U.S. Application Data

[62] Continuation of application No. 08/465,112, Jun. 5, 1995, Pat. No. 5,648,062, which is a division of application No. 08/256,151, filed as application No. PCT/EP93/00028, Jan. 8, 1993, Pat. No. 5,637,289.

[30] Foreign Application Priority Data

Jan. 9, 1992 [GB] United Kingdom .................. 9200391

[51] Int. Cl.$^6$ ........................ A61B 5/055; A61K 49/04; A61K 9/16
[52] U.S. Cl. ...................... 424/9.3; 424/9.32; 424/9.35; 424/9.4; 424/9.43; 424/9.52; 424/489; 424/493
[58] Field of Search .................... 424/9.52, 9.51, 424/9.5, 9.32, 489, 493, 9.35, 9.4, 9.43; 600/458, 420; 252/315.3; 106/162.1

[56] References Cited

U.S. PATENT DOCUMENTS

| | | | |
|---|---|---|---|
| 4,657,756 | 4/1987 | Rasor et al. | 424/9.52 |
| 5,141,738 | 8/1992 | Rasor et al. | 424/9.5 |
| 5,315,997 | 5/1994 | Widder et al. | 128/653.3 |

FOREIGN PATENT DOCUMENTS

| | | | |
|---|---|---|---|
| 0 458 745 | 11/1991 | European Pat. Off. | A61K 49/00 |

*Primary Examiner*—Jose' G. Dees
*Assistant Examiner*—Michael G. Hartley
*Attorney, Agent, or Firm*—Bacon & Thomas, PLLC

[57] ABSTRACT

The present invention relates to contrast agents comprising water-soluble microbubble-generating carbohydrate microparticles in admixture with at least 10% w/w relative to the overall composition of a non-surface active material which is less water soluble than the carbohydrate. The contrast agents exhibit useful levels of contrast efficiency and/or stability and may be used in diagnostic applications such as ultrasound and MR imaging.

13 Claims, No Drawings

CONTRAST AGENTS, CONSISTING OF CARBOHYDRATE PARTICLES

This application is a Continuation of application Ser. No. 08/465,112, filed Jun. 5, 1995 now U.S. Pat. No. 5,648,062, which is a Divisional of application Ser. No. 08/256,151, filed Nov. 1, 1994, now U.S. Pat. No. 5,637,289, which is a 371 of PCT/EP93/00028, filed Jan. 8, 1993.

This invention relates to novel contrast agents, more particularly to new microparticulate contrast agents of use in diagnostic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas microbubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas microbubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods or generating and/or stabilising gas microbubbles for echocardiography and other ultrasonic studies, for example using emulsifiers, oils, thickeners or sugars.

Techniques involving the use of sugars in ultrasound contrast agents are described in, for example, U.S. Pat. No. 4,681,119, U.S. Pat. No. 4,442,843 and U.S. Pat. No. 4,657,756, which disclose the use of particulate solids having a plurality of gas-filled voids and preferably also a plurality of nuclei for microbubble formation. EP-A-0123235 and EP-A-0122624 suggest ultrasound contrast agents consisting of surfactant-coated or surfactant-containing gas-containing microparticles which may include a variety of sugars. DE-A-3834705 proposes the use of suspensions containing microparticles of mixtures of at least one $C_{10-20}$ fatty acid with at least one non-surface active substance, including sugars such as cyclodextrins, monosaccharides, disaccharides or trisaccharides, as well as other polyols and inorganic and organic salts.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of X-ray imaging it has been observed that gases such as carbon dioxide may be used as negative oral contrast agents.

A disadvantage of many existing gas-containing/gas-generating particulate contrast agents such as the sugar-based agents discussed above is their relative lack of stability in vivo. This is a particular problem in applications such as echocardiography, where there is a need for improved contrast agents combining sufficient stability and small microbubble size (typically less than about 10 μm, preferably less than about 7 μm) to permit passage through the pulmonary capillary bed and so allow enhanced visualisation of the left side of the heart, preferably for more than one passage of circulation. There is accordingly a need for contrast agents which generate microbubble systems exhibiting good stability while still providing an effective level of contrast efficiency.

The present invention is based on our finding that contrast agents comprising microparticles of a water-soluble carbohydrate admixed with a substantial proportion (e.g. at least 10% w/w relative to the overall composition) of a less water-soluble non-surface active material may be used to generate microbubble systems exhibiting useful levels of contrast effect and/or stability. In the ultrasound field this may be demonstrated by, for example, in vitro measurements of initial attenuation levels and the half lives of the attenuative effect; a useful indication of the combined effect of these properties is the integral obtained by determining the area under the curve of a plot of attenuation against time.

Thus, according to one aspect of the present invention, there are provided contrast agents comprising water-soluble microbubble-generating carbohydrate microparticles in admixture with at least 10% w/w relative to the overall composition of a non-surface active material which is less water-soluble than the said carbohydrate.

The microparticulate carbohydrate may for example be selected from hexoses such as glucose, fructose or galactose; disaccharides such as sucrose, lactose or maltose; pentoses such as arabinose, xylose or ribose; and α-, β- and γ-cyclodextrins; the term "carbohydrate" as used herein is also intended to embrace sugar alcohols, e.g. alditols such as mannitol or sorbitol. Microparticles of the above carbohydrates will normally have gas present as an inclusion in the voids of their crystal structure and/or adhered to their surface, which gas may generate microbubbles when, for example, the microparticles are suspended or dissolved in an injectable carrier liquid, for example water for injection, an aqueous solution of one or more inorganic salts (e.g. physiological saline or a physiological buffer solution), an aqueous solution of a monosaccharide (e.g. glucose or galactose) or disaccharide (e.g. lactose), or an aqueous solution of a physiologically tolerable monohydric or polyhydric alcohol (e.g. ethanol, propanol, isopropanol, ethylene glycol, propylene glycol, glycerine or polyethylene glycol).

In addition to or alternatively to air, any biocompatible gas may be employed in the contrast agents of the invention, for example nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The term "gas" as used herein includes any substance in the gaseous form at 37° C. The gas may be contained in the contrast agent in such a way that before use the product is non-contrast giving but becomes effective on administration, e.g. as a result of the gas forming microbubbles as the soluble carbohydrate matrix dissolves.

Additionally or alternatively the carbohydrate may incorporate one or more gas precursors, including carbonates and bicarbonates (e.g. sodium or ammonium bicarbonate) and aminomalonate esters.

The non-surface active material may, for example, be a high molecular weight polysaccharide such as starch or dextran which exhibits lower water solubility than the microbubble-generating carbohydrate; a non-amphiphilic lipid such as a fatty acid ester or steroid acid ester; a fixed oil, fat or wax, for example a partially hydrogenated vegetable oil such as cottonseed oil or soyabean oil or a mixture thereof; a triglyceride, for example a glyceryl ester of a high molecular weight (e.g. $C_{10-50}$) aliphatic acid, such as glyceryl trilaurate or glyceryl trimyristate; a wax, for example beeswax or carnauba wax; or a mixture of such non-amphiphilic lipids. Alternatively or additionally a substantially completely water-insoluble material, e.g. an inorganic material such as silica or an iron oxide such as magnetite ($Fe_3O_4$) may be employed.

As indicated above, the non-surface active material will normally be present in an amount of at least 10% w/w, for example 20–80% w/w, advantageously 25–75% w/w., relative to the overall composition. The microparticulate carbohydrate and non-surface active material may conveniently be employed in substantially identical amounts by weight.

If desired, the contrast agents according to the invention may also contain small amounts (e.g. 0.01–5.0% w/w, preferably 0.1–2.0% w/w) of materials such as amphiphilic lipids in order to modify the solubility properties of the microparticles. Amphiphilic lipids which may be used for this purpose include fatty acids and salts (e.g. alkali metal salts) thereof, steroid acids, sterols, phospholipids and glycolipids. The amphiphilic lipid may, for example, be a high molecular weight (e.g. $C_{10-50}$) straight chain saturated or unsaturated aliphatic acid, such as capric, palmitic, hexadecanedioic, stearic, linolenic, behenic, docosanedioic or melissic acid; an aralkanoic acid, e.g. a phenyl lower alkanoic acid such as 2-phenylbutyric acid; a cholanic acid such as 5β-cholanic acid; salts of any of the foregoing acids; a high molecular weight (e.g. $C_{10-50}$) straight chain aliphatic alcohol such as stearyl alcohol or cetyl alcohol; a glyceride, for example a glyceryl ester of a high molecular weight (e.g. $C_{10-50}$) aliphatic acid, such as glyceryl monolaurate; cholesterol; a phospholipid such as phosphatidyl choline or dioleoylphosphatidyl ethanolamine; or a mixture thereof.

The contrast agents of the invention may be used in a variety of diagnostic imaging techniques, including ultrasound, MR and X-ray imaging. Their use in diagnostic ultrasonic imaging and in MR imaging, e.g. as susceptibility contrast agents, constitute preferred features of the invention.

The contrast agents of the invention may be prepared by any convenient method which leads to physical admixture of the carbohydrate and the less water-soluble non-surface active material and to production of microparticles of the desired size. Thus, for example, the contrast agents may be prepared simply by micronising a mixture of the two components, for example using conventional techniques such as grinding or milling. Alternatively the two components (optionally together with any further component or components such as the above-described lipids) may be mixed in solution, e.g. by mixing an aqueous solution of the carbohydrate and a solution of the less water-soluble non-surface active material in water or a water-miscible organic solvent as appropriate (together with any desired additive, e.g. a lipid dissolved in a water-miscible organic solvent, for example a lower alkanol such as ethanol), the solvent or solvents thereafter being removed (e.g. by evaporation under reduced pressure) to yield a mixture of the desired components which is thereafter micronised to yield the desired microparticles. It will be appreciated that all processing operations should be effected under sterile conditions.

In general micronisation may be effected using conventional techniques such as grinding or milling. Ball-milling has been found to be particularly advantageous, permitting the preparation of microparticlas in the form of aggregates (for example having an aggregate size of 20–125 micrometres, such as 30–50 micrometres) of particles having a particle size of, for example, 1–50 micrometres, such as 1–10 micrometres. Such aggregates will tend to contain a substantial volume of air adsorbed on their surfaces and entrained in voids such as interparticle cavities or at grain boundaries between the crystallites. The particle size may, for example, be selected to be substantially commensurate with the desired microbubble size. In ultrasonic applications such as echocardiography, in order to permit free passage through the pulmonary system and to achieve resonance with the preferred imaging frequencies of about 0.1–15 MHz, it may be convenient to employ microbubbles and microparticles having an average size of 0.1–10 μm, e.g. 1–7 μm; the use of microparticles of average size 1–4 μm to generate microbubbles with an average size of 4–7 μm is generally advantageous. Substantially larger bubbles and particles, e.g. with average sizes up to 500 μm, may however be useful in other applications, for example gastrointestinal imaging.

The following non-limitative Examples serve to illustrate the invention:

EXAMPLES 1–3

D-(+)-Galactose/Starch Mixtures

D-(+)-Galactose (Merck) in the amounts stated in Table I was mixed with starch (Reppal PSM 70, Reppe Glykos, Sweden) in the stated amounts and ground for 10 minutes under aseptic conditions in a stainless steel ball-mill having a 50 ml grinding cup and 3×20 mm balls (Retach centrifugal ball-mill, S1).

TABLE I

| Example No. | Amount of D-(+)-galactose (g) | Amount of starch (g) |
|---|---|---|
| 1 | 2.0 | 2.0 |
| 2 | 0.8 | 3.2 |
| 3 | 3.2 | 0.8 |

EXAMPLE 4

D-(+)-Galactose/Iron Oxide Mixture

Commercially available D-(+)-galactose (5.0 g) was mixed with commercially available magnetite ($Fe_3O_4$-5.0 g) and ground in a ball-mill as described in Examples 1–3.

EXAMPLE 5

D-(+)-Galactose/Starch/Palmitic Acid Mixture

D-(+)-Galactose (5.0 g) was dissolved in distilled water (7.1 g) at 60° C. and mixed with starch (5.0 g) dissolved in distilled water (30.0 g) at 60° C. Palmitic acid (0.02 g) was dissolved in 96% ethanol (1.2 g) and added with stirring to the carbohydrate solution at 60° C. The solvents were evaporated under reduced pressure (10 torr, 60° C.) and the resulting solid mixture was dried in a desiccator overnight prior to being ground in a ball-mill as described in Examples 1–3.

EXAMPLE 6 and 7

D-(+)-Galactose/Dextran Mixtures

D-(+)-Galactose in the amounts stated in Table II was dissolved in the stated weights of purified water at 50° C. Dextran (molecular weight ca. 20,000) in the stated amounts was similarly dissolved in the stated weights of purified water at 50° C. The solutions were sterile filtered (0.22 μm filter) and mixed with stirring, whereafter the solvent was evaporated under reduced pressure (10 torr, 40° C.). The resulting solid mixtures were dried in a desiccator overnight and then ground in a ball-mill as described in Examples 1–3.

TABLE II

| Example No. | Amount of D-(+)-galactose (g) | Weight of water used to dissolve D-(+)-galactose (g) | Amount of dextran (g) | Weight of water used to dissolve dextran (g) |
|---|---|---|---|---|
| 6 | 5.0 | 14.4 | 5.0 | 14.4 |
| 7 | 2.5 | 7.2 | 7.5 | 21.7 |

EXAMPLE 8

Echogenicity in vitro 10 ml of propylene glycol mixed with 90 ml of 5% dextrose in water was used as a carrier liquid for determining the echogenicity of products according to the Examples. 1.0 g of each product was dispersed in 3.0 ml of the carrier liquid and shaken for 15 seconds. The resulting mixture was added to 52 ml of 5% human serum albumin infusion solution in the measurement cell and the acoustic effects of the products were investigated by measuring the acoustic transmission through the samples using a 5 MHz broadband transducer in a pulse-reflection technique. The temperature in the measurement cell was stabilised to 37° C. and circulation of the liquid was maintained by means of stirring at a constant rate. Ultrasound transmission through the samples was measured as a function of time over a duration of 390 seconds. Results were normalized to measurements on a reference consisting of 55 ml of 5% human serum albumin infusion solution.

The products of the Examples generally showed higher echogenicity than the reference.

We claim:

1. A contrast agent comprising water-soluble microbubble-generating carbohydrate microparticles in admixture with at least 10% w/w relative to the overall composition of a non-surface active material which is less water-soluble than the said carbohydrate, said microparticles having average sizes substantially larger than 10μm, and up to 500μm and wherein said microparticles are in aggregate form.

2. A contrast agent as claimed in claim 1 in which the carbohydrate is a water-soluble pentose, hexose, disaccharide, cyclodextrin or sugar alcohol.

3. A contrast agent as claimed in claim 1 in which the non-surface active material is starch or dextran.

4. A contrast agent as claimed in claim 1 wherein said microbubbles are released after administration of the contrast agent and are contrast effective in the gastrointestinal system.

5. A contrast agent as claimed in claim 4 wherein said microbubbles comprise sulphur hexafluoride or a low molecular weight fluorinated hydrocarbon.

6. A contrast agent as claimed in claim 1 in which the non-surface active material is a water insoluble inorganic material.

7. A contrast agent as claimed in claim 6 in which the non-surface active material is an iron oxide.

8. A contrast agent as claim in claim 1 additionally containing an amphiphilic lipid so as to modify the solubility properties of the microparticles.

9. A contrast agent as claimed in claim 8 containing 0.1–2.0% w/w relative to the overall composition of an amphiphilic lipid selected from the group consisting of fatty acids and salts thereof, steroid acids, sterols, phospholipids and glycolipids.

10. A method of generating an enhanced diagnostic image of the gastrointestinal system of a human or non-human animal body comprising administering a diagnostic image enhancing amount of a contrast agent according to claim 1 to said body and generating an enhanced diagnostic image.

11. A method as claimed in claim 10 wherein the contrast agent is used as a negative oral X-ray contrast agent.

12. A method of generating an enhanced diagnostic ultrasonic image of the gastrointestinal system of a human or non-human animal body comprising administering a diagnostic image enhancing amount of a contrast agent according to claim 1 to said body and generating an enhanced diagnostic ultrasonic image.

13. A method of generating an enhanced magnetic resonance image of the gastrointestinal system of a human or non-human animal body comprising administering to said body a magnetic resonance image enhancing amount of a contrast agent according to claim 1 to said body and generating an enhanced magnetic resonance image.

* * * * *